(12) United States Patent
Lewis et al.

(10) Patent No.: US 8,467,854 B2
(45) Date of Patent: Jun. 18, 2013

(54) NEUROVASCULAR INTERVENTION DEVICE

(75) Inventors: Nickola Lewis, Fremont, CA (US); Scott Harshman, Livermore, CA (US); Charles Wells, Concord, CA (US); Daniel O'Keefe, San Francisco, CA (US); Robert Zelenka, Milpitas, CA (US); Richard Romley, Tracy, CA (US)

(73) Assignee: Scimed Life Systems, Inc., Maple Grove, MN (US)

( * ) Notice: Subject to any disclaimer, the term of this patent is extended or adjusted under 35 U.S.C. 154(b) by 1591 days.

(21) Appl. No.: 11/111,254

(22) Filed: Apr. 20, 2005

(65) Prior Publication Data
US 2006/0253023 A1 Nov. 9, 2006

(51) Int. Cl.
*A61B 5/05* (2006.01)

(52) U.S. Cl.
USPC ............ 600/427; 600/407; 600/410; 600/424

(58) Field of Classification Search
USPC ............................ 600/407, 410, 427; 604/526
See application file for complete search history.

(56) References Cited

U.S. PATENT DOCUMENTS

| | | | |
|---|---|---|---|
| 4,739,768 A | 4/1988 | Engelson | |
| 4,841,977 A | 6/1989 | Griffith et al. | |
| 4,994,069 A | 2/1991 | Ritchart et al. | |
| 5,095,911 A | 3/1992 | Pomeranz | |
| 5,321,501 A | 6/1994 | Swanson et al. | |
| 5,368,035 A | 11/1994 | Hamm et al. | |
| 5,464,016 A | 11/1995 | Nicholas et al. | |
| 5,554,139 A * | 9/1996 | Okajima | 604/526 |
| 5,637,086 A | 6/1997 | Ferguson et al. | |
| 5,697,967 A * | 12/1997 | Dinh et al. | 128/898 |
| 6,171,326 B1 * | 1/2001 | Ferrera et al. | 606/191 |
| 6,272,370 B1 * | 8/2001 | Gillies et al. | 600/411 |
| 6,290,668 B1 | 9/2001 | Gregory et al. | |
| 6,332,089 B1 * | 12/2001 | Acker et al. | 600/424 |
| 6,514,273 B1 | 2/2003 | Voss et al. | |
| 6,527,790 B2 * | 3/2003 | Chien et al. | 606/194 |
| 6,533,751 B2 * | 3/2003 | Cragg et al. | 604/93.01 |
| 6,638,245 B2 | 10/2003 | Miller et al. | |
| 6,702,782 B2 | 3/2004 | Miller et al. | |
| 6,730,037 B2 | 5/2004 | Jang | |

(Continued)

FOREIGN PATENT DOCUMENTS

EP 0993837 A 4/2000

OTHER PUBLICATIONS

Huang et al., "Optical Coherence Tomography," Science, 254, Nov. 22, 1991, pp. 1178-1181.

*Primary Examiner* — Unsu Jung
*Assistant Examiner* — Joel Lamprecht
(74) *Attorney, Agent, or Firm* — Frommer Lawrence & Haug LLP; Bruce E. Black

(57) ABSTRACT

The present invention generally relates to medical devices, and more particularly to an improved intravascular intervention device. In one embodiment, an intravascular intervention device includes a microcatheter configured for intravascular delivery, an imaging wire received within the microcatheter, and a treatment device received within the microcatheter, wherein the imaging wire and the treatment device may be simultaneously advanced. The treatment device is configured to perform intravascular intervention. For example, the treatment device may be configured to deliver a stent, an embolic coil and/or a thrombolytic agent. In this embodiment, the intravascular intervention device may image the area of interest while performing the intravascular intervention, thus allowing imaging to take place in real time.

24 Claims, 3 Drawing Sheets

U.S. PATENT DOCUMENTS

| | | |
|---|---|---|
| 6,770,035 B2 | 8/2004 | White et al. |
| 6,796,945 B2 | 9/2004 | Belef et al. |
| 7,329,223 B1 * | 2/2008 | Ainsworth et al. ........... 600/300 |
| 2002/0161342 A1 | 10/2002 | Rivelli et al. |
| 2002/0161394 A1 * | 10/2002 | Macoviak et al. ........... 606/200 |
| 2004/0176682 A1 | 9/2004 | Murphy |
| 2005/0080469 A1 * | 4/2005 | Larson et al. ................. 607/101 |
| 2005/0149008 A1 * | 7/2005 | Larson et al. .................... 606/27 |
| 2005/0165298 A1 * | 7/2005 | Larson et al. ................. 600/410 |
| 2006/0015126 A1 * | 1/2006 | Sher .............................. 606/159 |

* cited by examiner

NEUROVASCULAR INTERVENTION DEVICE

FIELD OF THE INVENTION

The field of the invention relates to medical devices, and more particularly to an neurovascular intervention device.

BACKGROUND OF THE INVENTION

Intraluminal, intracavity, intravascular, and intracardiac treatments and diagnosis of medical conditions utilizing minimally invasive procedures are effective tools in many areas of medical practice. These procedures are typically performed using diagnostic and interventional catheters that are inserted percutaneously into the arterial network and traversed through the vascular system to the site of interest. The diagnostic catheter may have imaging capability, typically an ultrasound imaging device, which is used to locate and diagnose a diseased portion of the body, such as a stenosed region of an artery. For example, U.S. Pat. No. 5,368,035, issued to Hamm et al., the disclosure of which is incorporated herein by reference, describes a catheter having an intravascular ultrasound imaging transducer.

Currently, there exists no indicated intravascular imaging method for the neurovasculature. When evaluating a proposed intravascular imaging device for the neurovasculature, the procedure steps for coronary interventions serve as baseline. Typically, for cardiovascular intervention, the use of the imaging device alternates with the use of the treatment device, i.e., a clinician would insert the imaging device to diagnose the area of interest, and then remove the imaging device to insert the appropriate treatment device. Applied to the neurovascular system this may be particularly undesirable due to time considerations in the treatment of strokes and/or intravascular aneurysms. In such cases, it may be desirable to provide simultaneous and/or real-time intra-lumen imaging of a patient's vasculature.

In the case of a stroke caused by embolus, it may be beneficial for the clinician to determine the nature of the embolus in order to plan necessary intervention. The embolus may come in two forms, hard plaque or soft thrombus, and different treatments may be used for each. For soft thrombus, drug treatment may be preferred, since it is a more conservative treatment, but such a treatment may be ineffective for hard plaque, which may require more aggressive treatments such as stent placement. The ability to make a quick assessment benefits the patient by receiving the most applicable intervention as soon as possible.

In the case of an aneurysm, the ability to characterize the aneurysm accurately is very important, particularly for embolic coiling procedures. The diameter of the neck of the aneurysm, the diameter of the aneurysm itself, the density of the sac thrombus, and the patency of the parent artery are all important items of data when planning intervention. The ability to determine and/or confirm these items of data real time may provide a factor of safety when planning the required intervention. For example, the embolic coils originally chosen for treatment based on angiograms may have to be modified based on findings that the aneurysm neck is larger or smaller than anticipated. Accordingly, an improved intravascular intervention device would be desirable.

SUMMARY OF THE INVENTION

The present invention generally relates to medical devices, and more particularly to an improved intravascular intervention device. In one embodiment, an intravascular intervention device includes a microcatheter configured for intravascular delivery, an imaging wire received within the microcatheter, and a treatment device received within the microcatheter, wherein the imaging wire and the treatment device may be simultaneously advanced. The treatment device is configured to perform intravascular intervention. For example, the treatment device may be configured to deliver a stent, an embolic coil and/or a thrombolytic agent. In this embodiment, the intravascular intervention device may image the area of interest while performing the intravascular intervention, thus allowing imaging to take place in real time.

Other systems, methods, features and advantages of the invention will be or will become apparent to one with skill in the art upon examination of the following figures and detailed description. It is intended that all such additional systems, methods, features and advantages be included within this description, be within the scope of the invention, and be protected by the accompanying claims.

BRIEF DESCRIPTION OF THE DRAWINGS

In order to better appreciate how the above-recited and other advantages and objects of the present inventions are obtained, a more particular description of the invention briefly described above will be rendered by reference to specific embodiments thereof, which are illustrated in the accompanying drawings. It should be noted that the components in the figures are not necessarily to scale, emphasis instead being placed upon illustrating the principles of the invention. Moreover, in the figures, like reference numerals designate corresponding parts throughout the different views. However, like parts do not always have like reference numerals. Moreover, all illustrations are intended to convey concepts, where relative sizes, shapes and other detailed attributes may be illustrated schematically rather than literally or precisely.

DETAILED DESCRIPTION OF THE PREFERRED EMBODIMENTS

Figure 1A:
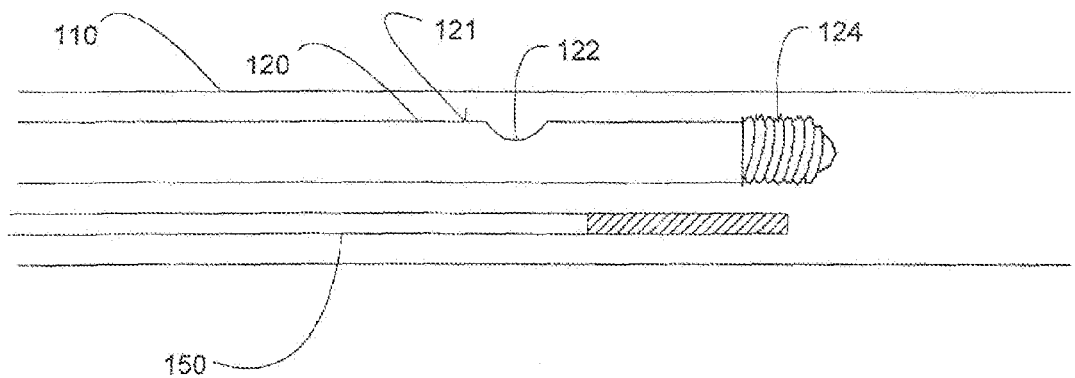
FIG. 1a is a cross-sectional side view of a microcatheter in accordance with a preferred embodiment of the present invention.

As described above, an intravascular intervention device that allows the simultaneous delivery of an imaging device and a treatment device may be desirable. Turning to FIG. 1a, a microcatheter 100 is shown. The microcatheter 100 is constructed to allow navigation into cerebral arteries. Such a microcatheter 100 has a size range of up to 0.027 inches. An example of such a microcatheter is described in U.S. Pat. No. 4,739,768 to Engelson, which is hereby incorporated by reference in its entirety. The microcatheter 100 includes an outer sheath 110 having a lumen that is capable of receiving an imaging wire 120 and a treatment device 150. The microcatheter 100 may utilize a guidewire (not shown) to facilitate in advancing the microcatheter 100 to the area of interest. One of ordinary skill in the art will appreciate that both the imaging wire 120 and the treatment device 150 may be capable of being advanced beyond the distal end of the sheath 110 of the microcatheter 100.

Figure 1B:
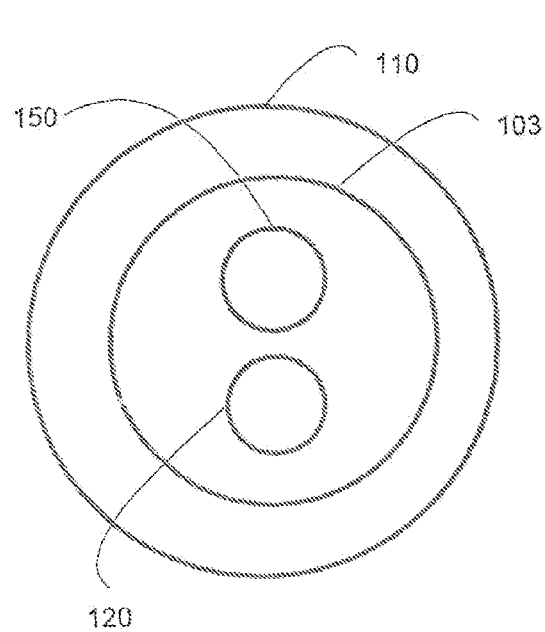
FIG. 1b is a cross-sectional view of a microcatheter in accordance with a preferred embodiment of the present invention.
Figure 1C:
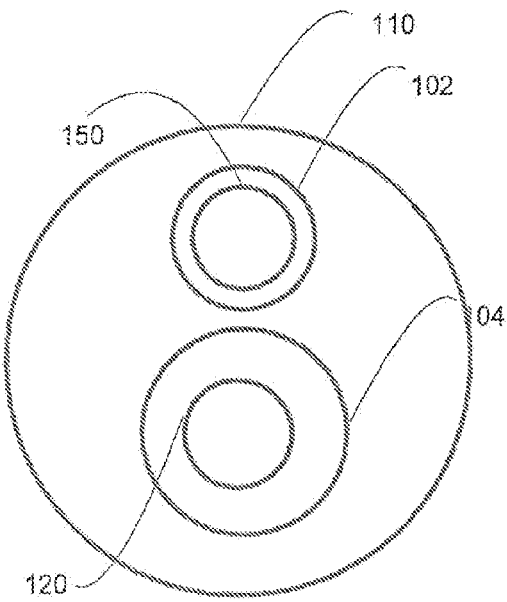
FIG. 1c is a cross-sectional view of a microcatheter in accordance with a preferred embodiment of the present invention.

Turning to FIG. 1b, which shows a cross-section of a microcatheter 100, the microcatheter 100 may receive the imaging wire 120 and the treatment device 150 via a single lumen 103. Alternatively, turning to FIG. 1c, which shows a cross-section of an alternative microcatheter 100, the microcatheter 100 may receive the imaging wire 120 and the treatment device 150 through a first lumen 102 and a second lumen 104 respectively.

Turning to back to FIG. 1a, the imaging wire 120 includes a sheath 121, preferably braided polymer, that is coupled with a floppy tip 124 at the distal end of the sheath 121. The sheath 121 includes a lumen that receives an imaging transducer assembly 130 shown in FIG. 2a. The imaging wire sheath 121 may be coated with a lubricious coating that enables improved movement within a vessel. The imaging sheath 121 preferably includes a puncture hole 122 towards the distal portion of the imaging wire 120, which allows blood pressure to fill the cavity around the imaging element 130 to improve imaging. The sheath braid may discontinue for a particular amount of length, thus allowing the imaging transducer to acquire an image with reduced interference. The sheath 121 may be withdrawn completely after reaching the desired position, thus leaving the imaging transducer assembly 130 and the floppy tip 124 exposed to the area of interest. In such a configuration, it may be desirable to coat the assembly 130 with a lubricious and/or thrombolytic agent, such as heparin.

Figure 3:
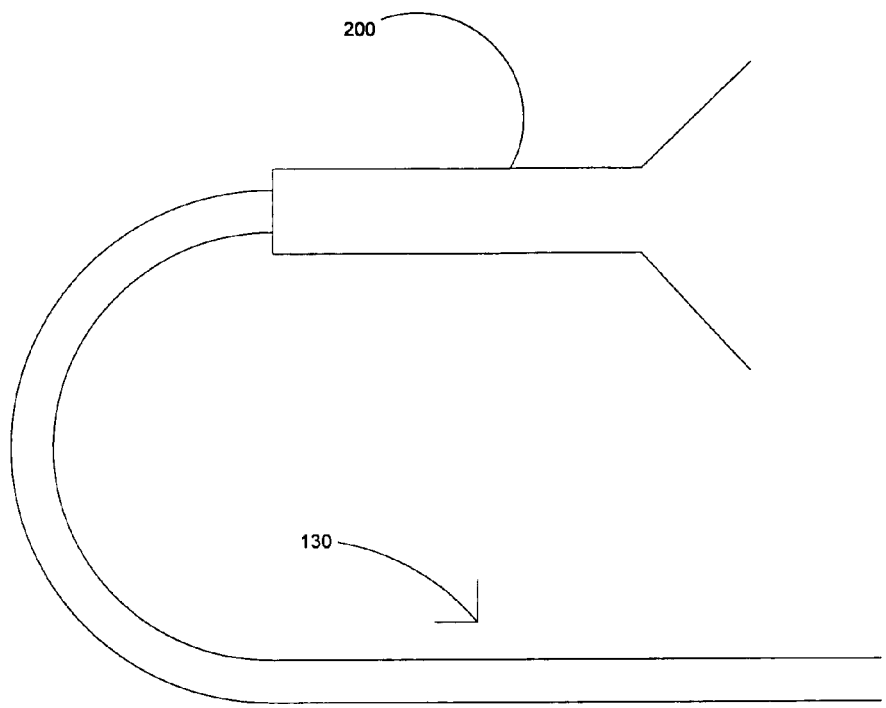
FIG. 3 is a cross-sectional view of an imaging wire in accordance with a preferred embodiment of the present invention.

In an alternative configuration, the sheath 121 may be a thick walled hypotube or partially hollowed rod to allow attachment of the floppy tip 124 and passage of the imaging transducer assembly 130. In addition, the sheath 121 may include conductive traces that allow the imaging transducer assembly 130 to be electrically coupled with a proximal connector 200 (shown in FIG. 3). A thin coating of insulating material may protect the conductive traces.

The floppy tip 124 may be composed of a layered coil atop a cylindrical wire that is flattened into a ribbon under the coil. Further, the floppy tip 124 may have a proximally extended axial section over which the imaging transducer 130 may translate (not shown).

Figure 2A:
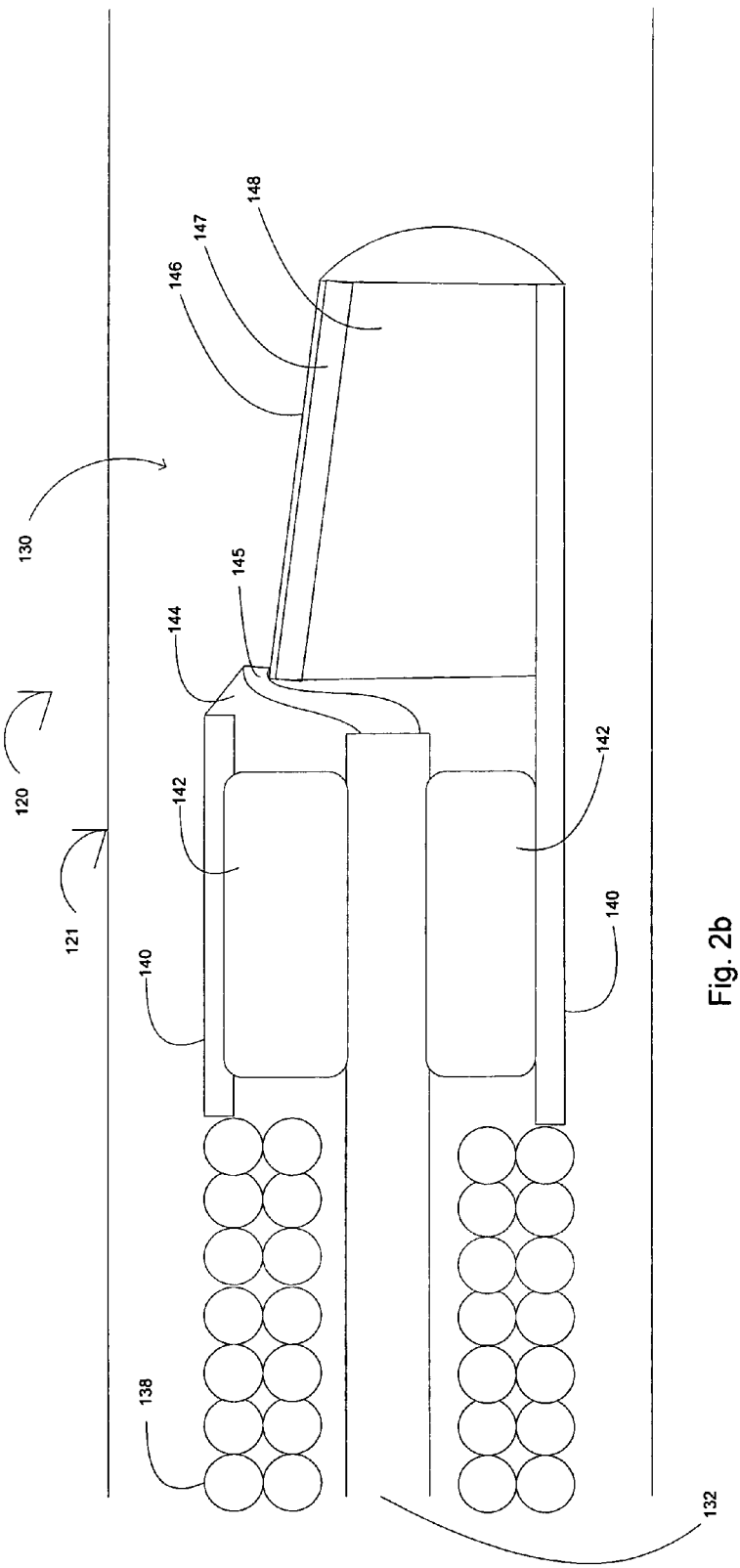
FIG. 2a is a cross-sectional side view of an imaging wire in accordance with a preferred embodiment of the present invention.
Figure 2B:
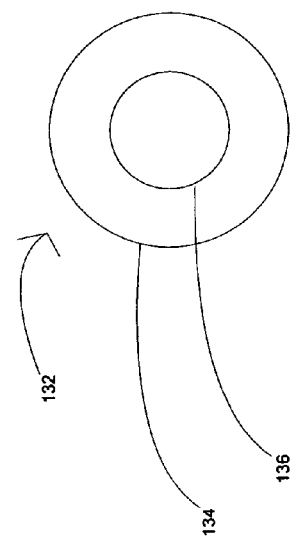
FIG. 2b is a cross-sectional view of an imaging wire in accordance with a preferred embodiment of the present invention.

Turning to FIG. 2a, an example of an imaging transducer assembly 130 is shown within the sheath 121 of the imaging wire 120. The imaging transducer 130 includes a coaxial cable 132, having a center conductor wire 136 and an outer shield wire 134, shown in FIG. 2b. A conductive wire, having a diameter of approximately 500 microns, is wrapped around the coaxial cable 132, forming a coil, which functions as a drive shaft 138. The wire may be a laser cut Nitinol tube, which allows for torquability and flexibility. Alternatively, the drive shaft 138 may be composed of coaxial cables wound such that the cables are kept separated, via individual shielding or additional wire, while surrounding a neutral core. Further, the drive shaft 138 may be pre-tensioned.

Connected to the distal end of the drive shaft 138 is a stainless steel housing 140, which serves to reinforce the structure of the imaging transducer assembly 130. Surrounding the coaxial cable 132, within the housing 140 is a silver epoxy 142, a conductive material. Thus, the housing 140 is electrically coupled to the shield wire 134 of the coaxial cable 132 via the epoxy 142. On the distal end of the silver epoxy 142 is an insulating substance, e.g., a non-conductive epoxy 144.

Figure 4:
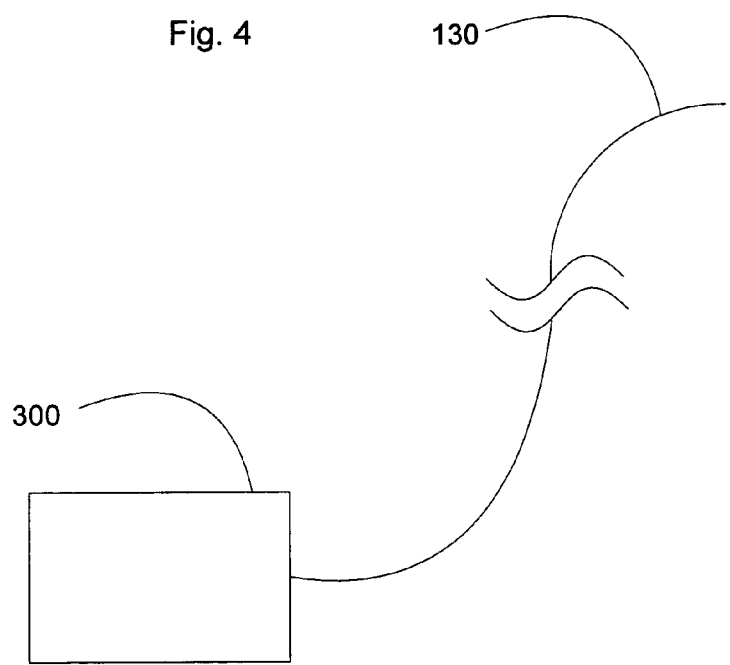
FIG. 4 is a diagram of a medical imaging system in accordance with a preferred embodiment of the present invention.

Alternatively, or in addition to the configuration above, the drive shaft 138 may be printed with one or more conductive traces that allow communication between the imaging transducer 130 and a proximal connector 200 (shown in FIG. 3), which allows the imaging transducer 130 to connect to external circuitry 300 that processes signals, such as imaging and navigational signals, from the imaging transducer 130, such circuits being well known (shown in FIG. 4). In yet another alternative configuration, the drive shaft 138 may be composed of an extruded polymer reinforced with a polymer/fiber/metal braid with the coaxial cable 132 extruded within the walls (not shown).

On the distal end of the non-conductive epoxy 144 is a layer of piezoelectric crystal ("PZT") 147, "sandwiched" between a conductive acoustic lens 146 and a conductive backing material 148, formed from an acoustically absorbent material (e.g., an epoxy substrate having tungsten particles). The acoustic lens 146 is electrically coupled with the center conductor wire 136 of the coaxial cable 132 via a connector 145 that is insulated from the silver epoxy 142 and the backing material 148 by the non-conductive epoxy 144. The acoustic lens 146 may be non-circular and/or have a convex surface. The backing material 148 is connected to the steel housing 140. It is desirable for the imaging transducer assembly 130 to be surrounded by a sonolucent media. The sonolucent media may be saline. Alternatively, or in addition to, as mentioned above, the sheath 121 of the imaging wire 120 may include a puncture hole 122 to allow blood to surround the imaging transducer assembly 130 as well. As one of ordinary skill in the art may appreciate, the imaging transducer assembly 130 may be translatable relative to the floppy tip 124. Further, the floppy tip 124 may be detachable, thereby exposing the imaging transducer assembly 130.

During operation, the PZT layer 147 is electrically excited by both the backing material 148 and the acoustic lens 146. The backing material 148 receives its charge from the shield wire 134 of the coaxial cable 132 via the silver epoxy 142 and the steel housing 140, and the acoustic lens 146, which may also be silver epoxy, receives its charge from the center conductor wire 136 of the coaxial cable 132 via the connector 145, which may be silver epoxy as well.

In an alternative embodiment, transducer 130 is replaced by a phased array as disclosed in Griffith et al., U.S. Pat. No. 4,841,977, which is hereby incorporated by reference in its entirety. Further, other imaging devices may be used, instead of, or in addition to imaging transducers, such as light based apparatuses for obtaining images through optical coherence tomography (OCT). Image acquisition using OCT is described in Huang et al., "Optical Coherence Tomography," Science, 254, Nov. 22, 1991, pp 1178-1181, which is hereby incorporated by reference in its entirety. A type of OCT imaging device, called an optical coherence domain reflectometer (OCDR) is disclosed in Swanson U.S. Pat. No. 5,321, 501, which is incorporated herein by reference. The OCDR is capable of electronically performing two- and three-dimensional image scans over an extended longitudinal or depth range with sharp focus and high resolution and sensitivity over the range.

Turning to the treatment device 150 shown in FIG. 1a, the treatment device 150 delivers treatment to an intravascular area, such as an area with an aneurysm or an embolism. One of ordinary skill in the art may appreciate that the treatment device 150 may deliver drugs, agents, or medical devices such as embolic coils or stents. U.S. Pat. No. 4,994,069 to Ritchart, entitled "Vaso-Occlusion Coil and Method," the entirety of which is hereby incorporated by reference, describes a treatment device that delivers one or more vaso-occlusive coils.

In the foregoing specification, the invention has been described with reference to specific embodiments thereof. It will, however, be evident that various modifications and changes may be made thereto without departing from the broader spirit and scope of the invention. For example, the reader is to understand that the specific ordering and combination of process actions described herein is merely illustrative, and the invention can be performed using different or additional process actions, or a different combination or ordering of process actions. As a further example, each feature of one embodiment can be mixed and matched with other features shown in other embodiments. Additionally and obviously, features may be added or subtracted as desired. Accordingly, the invention is not to be restricted except in light of the attached claims and their equivalents.

What is claimed is:

1. An intravascular intervention device comprising:
    a microcatheter configured to fit in a patient's neurovasculature, wherein the microcatheter has a diameter equal to or less than 0.027 inches;
    an imaging wire received within the microcatheter, the imaging wire comprising an imager configured to image the neurovasculature; and
    a treatment device received within the microcatheter and positioned to one side of the imaging wire, the treatment device being adapted to apply treatment to the neurovasculature, wherein the microcatheter is configured to simultaneously receive the imaging wire and the treatment device.

2. The device of claim 1, wherein the microcatheter includes a sheath having a lumen configured to receive the imaging wire and the treatment device.

3. The device of claim 1, wherein the microcatheter includes a sheath having first and second lumens, wherein each lumen is configured to receive one of the imaging wire and the treatment device.

4. The device of claim 1, wherein the treatment device is configured to deliver an embolic coil.

5. The device of claim 1, wherein the treatment device is configured to deliver a treatment drug.

6. The device of claim 1, wherein the treatment device is configured to deliver a stent.

7. The device of claim 1, wherein the imaging wire and the treatment device are aligned along different longitudinal axes, and are parallel at a distal end of the microcatheter.

8. The device of claim 1, wherein the imaging wire is received via a first lumen and the treatment device is received via a second lumen within the microcatheter, wherein the first and second lumens are separated.

9. The device of claim 1, wherein the imaging wire and the treatment device are received via a single lumen within the microcatheter.

10. The device of claim 1, wherein the imaging wire and the treatment device are parallel and side-by-side.

11. An intravascular intervention device comprising:
    a microcatheter configured to fit in a patient's neurovasculature;
    an imaging wire received within the microcatheter, the imaging wire comprising an imager configured to image the neurovasculature, wherein the imaging wire includes a sheath and a floppy tip coupled to the distal end of the sheath; and
    a treatment device received within the microcatheter and positioned to one side of the imaging wire, the treatment device being adapted to apply treatment to the neurovasculature, wherein the microcatheter is configured to simultaneously receive the imaging wire and the treatment device.

12. The device of 11, wherein the sheath defines a vent hole towards the distal end of the sheath.

13. The device of claim 11, wherein the imaging wire includes an imaging transducer assembly received within the sheath of the imaging wire.

14. An intravascular intervention system, comprising:
    an intravascular device comprising
    a microcatheter configured to fit in a patient's neurovasculature;
    an imaging wire received within the microcatheter, the imaging wire comprising an imager configured to image the neurovasculature, wherein the imaging wire includes a sheath and a floppy tip coupled to the distal end of the sheath; and
    a treatment device received within the microcatheter and positioned to one side of the imaging wire, wherein the microcatheter is configured to simultaneously receive the imaging wire and the treatment device; and
    a processor coupled to the imaging wire configured to process signals generated by the imaging wire.

15. The system of claim 14, wherein the microcatheter includes a sheath having a lumen configured to receive the imaging wire and the treatment device.

16. The system of claim 14, wherein the microcatheter includes a sheath having first and second lumens, wherein each lumen is configured to receive one of the imaging wire and the treatment device.

17. The system of claim 14, wherein the sheath defines a puncture hole towards the distal end of the sheath.

18. The system of claim 14, wherein the imaging wire includes an imaging transducer assembly received within the sheath of the imaging wire.

19. The system of claim 18, wherein the imaging transducer assembly is translatable within the sheath of the imaging wire.

20. The system of claim 19, wherein the imaging wire further includes a drive shaft proximally coupled to the imaging transducer assembly.

21. The device of claim 14, wherein the treatment device is configured to deliver a vaso-occlusive coil.

22. The device of claim 14, wherein the treatment device is configured to deliver a treatment drug.

23. The device of claim 14, wherein the treatment device is configured to deliver a stent.

24. An intravascular intervention device comprising:
    a microcatheter configured to fit in a patient's neurovasculature;
    a drive shaft;
    an imaging wire received within the microcatheter, the imaging wire comprising an imager configured to image the neurovasculature, wherein only the imaging wire is coupled to the drive shaft; and
    a treatment device received within the microcatheter and positioned to one side of the imaging wire, the treatment device being adapted to apply treatment to the neurovasculature, wherein the microcatheter is configured to simultaneously receive the imaging wire and the treatment device.

* * * * *